United States Patent
Chaung et al.

(10) Patent No.: US 12,383,613 B2
(45) Date of Patent: Aug. 12, 2025

(54) RECOMBINANT ANTIGEN AND METHOD OF MAKING THE SAME, ISOLATED POLYNUCLEOTIDE OF PORCINE REPRODUCTIVE AND RESPIRATORY SYNDROME VIRUS (PRRSV) AND IMMUNOGENIC COMPOSITION INCLUDING THE SAME

(71) Applicant: National Pingtung University of Science and Technology, Neipu (TW)

(72) Inventors: Hso-Chi Chaung, Neipu (TW); Ko-Tung Chang, Neipu (TW); Mei-Li Wu, Neipu (TW); Wen-Bin Chung, Neipu (TW)

(73) Assignee: NATIONAL PINGTUNG UNIVERSITY OF SCIENCE AND TECHNOLOGY, Neipu (TW)

( * ) Notice: Subject to any disclaimer, the term of this patent is extended or adjusted under 35 U.S.C. 154(b) by 576 days.

(21) Appl. No.: 17/930,168

(22) Filed: Sep. 7, 2022

(65) Prior Publication Data
US 2023/0074637 A1    Mar. 9, 2023

(30) Foreign Application Priority Data
Sep. 8, 2021   (TW) ................................ 110133470

(51) Int. Cl.
*A61K 39/12*    (2006.01)
*C12N 15/85*    (2006.01)
*A61K 39/00*    (2006.01)

(52) U.S. Cl.
CPC .............. *A61K 39/12* (2013.01); *C12N 15/85* (2013.01); *A61K 2039/552* (2013.01)

(58) Field of Classification Search
CPC ....................................................... A61K 39/12
See application file for complete search history.

(56) References Cited

FOREIGN PATENT DOCUMENTS

| TW | I554609 B | 10/2016 |
|----|-----------|---------|
| WO | 2016021276 A1 | 2/2016 |

OTHER PUBLICATIONS

Qian M. Cao, et al., Cytotoxic T lymphocyte epitopes identified from a contemporary strain of porcine reproductive and respiratory syndrome virus enhance CD4+CD8+ T, CD8+ T, and γδ T cell responses, Virology, Sep. 17, 2019, pp. 35-44, vol. 538.

*Primary Examiner* — Prema M Mertz
(74) *Attorney, Agent, or Firm* — Lippes Mathias LLP

(57) ABSTRACT

The present invention relates to a recombinant antigen and an isolated polynucleotide of porcine reproductive and respiratory syndrome virus (PRRSV), a composition including the same and a method of making the same. The recombinant antigen is a chimeric protein of PRRSV dual structural proteins and T-cell epitope. The polynucleotide encodes an amino acid sequence of the recombinant antigen. The recombinant protein expressed by the polynucleotide in an eukaryotic expression system can be beneficial for mass production and purification. An immunogenic composition including the recombinant antigen can promote pro-inflammatory M1-phenotype polarization of porcine alveolar macrophages (PAMs), reduce receptor CD163 expression that is mediated for viral entry and activate T helper (Th1) immune responses, thereby being applied to a vaccine composition against PRRSV.

16 Claims, 10 Drawing Sheets
Specification includes a Sequence Listing.

SEQUENCE LISTING

```
Sequence total quantity: 13
SEQ ID NO: 1              moltype = AA   length = 465
FEATURE                   Location/Qualifiers
REGION                    1..465
                          note = PRRSV recombinant antigen A1 (gp6Ld10T)
source                    1..465
                          mol_type = protein
                          organism = synthetic construct
SEQUENCE: 1
MLLVNQSHQG FNKEHTSKMV SAIVLYVLLA AAAHSAFAAD GTGMGSSLDD FCNDSTAPQK   60
VLLAFSITYT PVMIYALKVS RGRLLGLLHL LIFLNCAFTF GYMTFVHFES TNRVALTMGA  120
VVALLWGVYS AIETWKFITS RCRLCLLGRK YILAPAHHVE SAAGFHPIAA NDNHAFVVRR  180
PGSTTVNGTL VPGLKSLVLG GRKAVKQGVV NLVKYAKDGG GSGTASRSMC SRLLFLWCIV  240
PFYLAVLANA SNNNSSHIQL IYNLTLCELN GTDWLAQNFD WAVETFVIFP VLTHIVSYGA  300
LTTSHFLDTV GLATVSTAGY YHGRYVLSSI YAVCALAALI CFVIRLAKNC MSWRYSCTRY  360
TNFLLDTKGR LYRWRSPVIV EKRGKVEVGG HLIDLKRVVL DGSAATPLTR VSAEQWGRLH  420
MACLAALICF VIRLAKNCGG GSKGRLYRWR SPVIVEKACH HHHHH               465

SEQ ID NO: 2              moltype = DNA   length = 1398
FEATURE                   Location/Qualifiers
misc_feature              1..1398
                          note = recombinant gene sequence of PRRSV recombinant
                          antigen A1
source                    1..1398
                          mol_type = other DNA
                          organism = synthetic construct
SEQUENCE: 2
atgctgctcg tcaaccagtc gcaccaagga ttcaacaagg aacacacctc aaagatggtg     60
tcggctatcg ttctgtacgt gttgctggct gccgctgccc actctgcttt cgctgctgac    120
ggtaccggca tggggtcctc tctcgacgat ttctgcaacg attcaactgc tccacagaag    180
gtcctcttgg cctttctcga tcacttacaca ccggtcatga tctacgctct gaaggttagc   240
aggggtagac tgctcggctt gctgcacctc ttgatcttcc tcaactgcgc cttcaccttc    300
ggctacatga cttttcgtcca cttcgagtca actaacaggg ttgctctgac aatgggtgct   360
gtggtggctc tgctctgggg cgtctactct gccatcgaaa catggaagtt catcaccagc    420
cgttgtcgcc tgtgcttgct gggccgcaag tacatcctgg ctcctgctca ccacggggag   480
tccgctgccg gattccaccc tatcgctgcc aacgacaacc acgctttcgt tgtgcgtcgc   540
ccaggttcca ccactgtcaa cggcaccttg gttccggacc tgaagtcttt ggtgctgggt   600
ggccgtaagg ccgtcaagca aggcgtcgtt aacctggtga agtacgctaa ggatggaggt   660
ggcagcggta ccgctagcag atctatgtgc tcacgcctct tgttcctgtg gtgcatcgtt   720
cccttctacc tggccgtgct cgctaacgcc tccaacaaca acagctcaca catccagctg   780
atctacaacc tcaccttgtg cgagttgaac ggtactgact ggctggctca aaacttcgat   840
tgggccgtcg aaacattcgt tatcttccct gtgttgaccc acatcgtcag ctacggcgct   900
ctgcaaacct cacacttcct ggacaccgtg ggactgcta ccgtctctac tgccggatac    960
taccacggtc gttacgtttt tgtcgtccatc tacgctgtgt gtgccttggc tgccctgatc  1020
tgcttcgtga tcagactcgc taagaactgt atgtcctggc gttactcttg cacacgctac  1080
accaacttcc tgctcgacac taagggtagg ctgtacaggt ggagatcccg agtcatcgtt  1140
gagaagagag gcaaggtgga agtcggaggt cacctcatcg acttgaagcg cgtggtcctc  1200
gatgatcgg ctgccactcc tttgacaagg gtctccgctg aacaatgggg tcgtctccat  1260
atggcatgcc tggctgccct catctgcttc gtgattcgtc tcgctaaaaa ctgcggcgga  1320
ggttccaagg gccgcttgta cagatggagg tcgcccgtta tcgttgagaa ggcatgccac  1380
caccaccacc accactaa                                                1398
```

```
SEQ ID NO: 3           moltype = AA  length = 197
FEATURE                Location/Qualifiers
REGION                 1..197
                       note = PRRSV recombinant antigen A2 (lipo-M5Nt)
source                 1..197
                       mol_type = protein
                       organism = synthetic construct
SEQUENCE: 3
MKKLLIAAMM AAALAACSQE AKQEVKEAVQ AVESDVKDTA GSGSSLDDFC HDSTAPQKVL    60
LAFSITYTGP GPANNNSSSH LQLIYNLTLC ELNGTDWLAN KFDWGPGPKK NKKKNPEKPH   120
FPLATEDDVR HHFTPSERQL CLSSIQTAFN QGAGTCTLSD SGRISYTVEF SLPTHHTVRL   180
IRVTASPSAL EHHHHHH                                                  197

SEQ ID NO: 4           moltype = DNA  length = 25
FEATURE                Location/Qualifiers
misc_feature           1..25
                       note = forward primer of porcine IL-6 gene
source                 1..25
                       mol_type = other DNA
                       organism = synthetic construct
SEQUENCE: 4
gctgcttctg gtgatggcta ctgcc                                          25

SEQ ID NO: 5           moltype = DNA  length = 25
FEATURE                Location/Qualifiers
misc_feature           1..25
                       note = reverse primer of porcine IL-6 gene
source                 1..25
                       mol_type = other DNA
                       organism = synthetic construct
SEQUENCE: 5
tgaaactcca caagaccggt ggtga                                          25

SEQ ID NO: 6           moltype = DNA  length = 23
FEATURE                Location/Qualifiers
misc_feature           1..23
                       note = forward primer of porcine TNF- gene
source                 1..23
                       mol_type = other DNA
                       organism = synthetic construct
SEQUENCE: 6
atgagcactg agagcatgat ccg                                            23

SEQ ID NO: 7           moltype = DNA  length = 21
FEATURE                Location/Qualifiers
misc_feature           1..21
                       note = reverse primer of porcine TNF- gene
source                 1..21
                       mol_type = other DNA
                       organism = synthetic construct
SEQUENCE: 7
cctcgaagtg cagtaggcag a                                              21

SEQ ID NO: 8           moltype = DNA  length = 22
FEATURE                Location/Qualifiers
misc_feature           1..22
                       note = forward primer of porcine Arg-1 gene
source                 1..22
                       mol_type = other DNA
                       organism = synthetic construct
SEQUENCE: 8
agcccgtgtc aacatgactt cc                                             22

SEQ ID NO: 9           moltype = DNA  length = 21
FEATURE                Location/Qualifiers
misc_feature           1..21
                       note = reverse primer of porcine Arg-1 gene
source                 1..21
                       mol_type = other DNA
                       organism = synthetic construct
SEQUENCE: 9
ttgtgttggc atctttactg a                                              21

SEQ ID NO: 10          moltype = DNA  length = 20
FEATURE                Location/Qualifiers
misc_feature           1..20
                       note = forward primer of porcine IL-12 gene
```

```
source                  1..20
                        mol_type = other DNA
                        organism = synthetic construct
SEQUENCE: 10
ctcccacacc gaagcttgaa                                                    20

SEQ ID NO: 11           moltype = DNA  length = 18
FEATURE                 Location/Qualifiers
misc_feature            1..18
                        note = reverse primer of porcine IL-12 gene
source                  1..18
                        mol_type = other DNA
                        organism = synthetic construct
SEQUENCE: 11
ttcttcacca tgggggct                                                      18

SEQ ID NO: 12           moltype = DNA  length = 19
FEATURE                 Location/Qualifiers
misc_feature            1..19
                        note = forward primer of porcine -actin gene
source                  1..19
                        mol_type = other DNA
                        organism = synthetic construct
SEQUENCE: 12
acagacagcc gtgtgttcc                                                     19

SEQ ID NO: 13           moltype = DNA  length = 20
FEATURE                 Location/Qualifiers
misc_feature            1..20
                        note = reverse primer of porcine -actin gene
source                  1..20
                        mol_type = other DNA
                        organism = synthetic construct
SEQUENCE: 13
accttcacca tcgtgtctca                                                    20
```

RECOMBINANT ANTIGEN AND METHOD OF MAKING THE SAME, ISOLATED POLYNUCLEOTIDE OF PORCINE REPRODUCTIVE AND RESPIRATORY SYNDROME VIRUS (PRRSV) AND IMMUNOGENIC COMPOSITION INCLUDING THE SAME

RELATED APPLICATION

This application claims priority to Taiwan Application Serial Number 110133470, filed Sep. 8, 2021, which is herein incorporated by reference in its entirety.

BACKGROUND

The Sequence Listing XML associated with this application is filed in electronic format via EFS-Web and is hereby incorporated by reference into the specification in its entirety. The file name of the Sequence Listing XML is "SP-5436-US_SEQ_LIST.xml", created on Sep. 2, 2022, with a file size of 19,662 bytes.

FIELD OF INVENTION

The present invention relates to a recombinant protein of animal virus and a use thereof. More specifically, the present invention to a recombinant antigen having porcine reproductive and respiratory syndrome virus (PRRSV) dual structural protein and T-cell epitope, a method of making the same, an isolated polynucleotide thereof and an immunogenic composition including the same.

DESCRIPTION OF RELATED ART

Porcine Reproductive and Respiratory Syndrome Virus (PRRSV) is a positive single-stranded RNA virus, which has been classified to the Porartevirus genus, belonging to the order Nidovirales and the Arteriviridae family. PRRSV infections can cause reproductive disorder in sows and respiratory diseases in growing pigs, resulting in one of the most severe diseases in swine worldwide.

PRRSV vaccines have been utilized since the mid-1990s. Currently, there are four commercially available PRRSV vaccines, live-attenuated (e.g., modified live virus, MLV) vaccines, inactive virus (KIV) vaccines, subunit vaccines and nucleic acid vaccines (e.g., DNA vaccines, viral vector-based vaccines), for example. Although the live-attenuated vaccines can simultaneously induce cellular and humoral immune responses, their neutralizing antibody titers are much less so that they provide less protection against the heterologous viruses, causing the risks of virus shedding and reverting to a virulent form. The inactive virus vaccines are safer without the risk of reverting to a virulent form; however, they only induce humoral immune response, which require twice vaccination to induce sufficient protection, but they have no protection against heterologous viruses. That is to say, either the inactive virus vaccines or the live-attenuated vaccines cannot prevent or control PRRS.

The subunit vaccines and the nucleic acid vaccines have improved the above disadvantages and increase protection ability to heterologous viruses. However, the development of the subunit vaccines and the nucleic acid vaccines is mainly focused on ORF5, PPRSV can induce very complicated immune responses in the host, and PPRSV has developed diverse mechanisms to evade the host immune system, causing the difficulties in the development of the PPRSV vaccines.

SUMMARY

Accordingly, an aspect of the invention provides an immunogenic composition, which comprises a porcine reproductive and respiratory syndrome virus (PRRSV) recombinant antigen as an effective ingredient, wherein the PRRSV recombinant antigen is a chimeric protein of PRRSV dual structural proteins and T-cell epitope, thereby promoting polarization of porcine alveolar macrophages (PAMs) and activating T helper (Th1) immune responses.

Moreover, another aspect of the invention also provides an immunogenic composition, which comprises an isolated polynucleotide as an effective ingredient, and the isolated polynucleotide encodes an amino acid sequence of the aforementioned recombinant antigen.

Furthermore, a further aspect of the invention also provides a method of making a recombinant antigen of PRRSV, in which the aforementioned polynucleotide sequence is transfected into an eukaryotic expression system and then the recombinant antigen is expressed, for facilitating mass production and purification.

According to the aforementioned aspect, the invention provides an immunogenic composition, which includes a PRRSV recombinant antigen as an effective ingredient. The PRRSV recombinant antigen can be a chimeric protein of PRRSV dual structural proteins and T-cell epitope, and it can be consisted of an amino acid sequence listed as SEQ ID NO: 1.

In the aforementioned embodiment, the immunogenic composition can be, for example, an immunogenic composition against the PRRSV, a vaccine composition against the PRRSV, an immunogenic composition for promoting polarization of a porcine alveolar macrophage (PAM) and an immunogenic composition for activating Th1 immune responses. In an example, the PAM can be classified into a pro-inflammatory M1 phenotype, for example. In another example, the immunogenic composition can reduce a receptor CD163 expression for viral entry and activating Th1 immune responses.

According to another aforementioned aspect, the invention provides an immunogenic composition, which includes an isolated polynucleotide as an effective ingredient. The isolated polynucleotide can be consisted of a polynucleotide sequence listed as SEQ ID NO: 2, for encoding an amino acid sequence listed as SEQ ID NO: 1.

According to the further aforementioned aspect, the invention provides a method of making a recombinant antigen of PRRSV. In an embodiment, firstly, a polynucleotide sequence listed as SEQ ID NO: 2 can be transfected into an eukaryotic expression system. Next, the transfected eukaryotic expression system can be cultured for expressing the recombinant antigen, in which the recombinant antigen is an amino acid sequence listed as SEQ ID NO: 1. And then, a cultured supernatant of the transfected eukaryotic expression system is purified for obtaining the recombinant antigen.

In the aforementioned embodiment, the eukaryotic expression system can be a baculovirus expression system, for example.

With application to the recombinant antigen and the isolated polynucleotide of porcine reproductive and respiratory syndrome virus (PRRSV), the composition including the same and the method of making the same, the recombinant protein can be expressed by the eukaryotic expression system, for facilitating mass production and purification. The immunogenic composition including the recombinant antigen can promote pro-inflammatory M1-phenotype polarization of PAMs, reduce receptor CD163 expression mediated for viral entry and activate Th1 immune responses, thereby being applied to a vaccine composition against PRRSV.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1A:
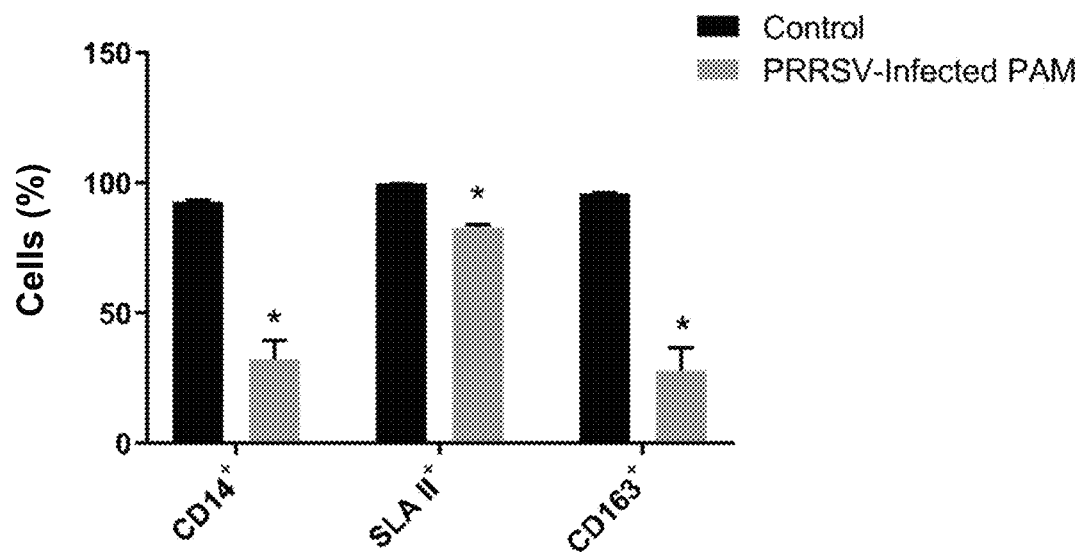
FIGS. 1A and 1B respectively illustrate the bar charts of cell percentages (FIG. 1A) and mean fluorescence intensity (MFI, FIG. 1B) of CD14, SLA II, CD80 and CD163-positive cells detected by flow cytometry according to an embodiment of the present invention.

If a term defined or used in a reference is inconsistent or opposite as it is defined or used herein, the definition of the term herein, other than that in the reference, is preferably applicable. Moreover, unless otherwise defined in the context, a singular term can include a plural one, and a plural term can also include a singular one.

As aforementioned, the present invention provides a recombinant antigen and an isolated polynucleotide of porcine reproductive and respiratory syndrome virus (PRRSV), a composition including the same and a method of making the same. The recombinant antigen is a chimeric protein of PRRSV dual structural proteins and T-cell epitope. An immunogenic composition including the recombinant antigen can promote polarization of porcine alveolar macrophages (PAMs), reduce PAMs surface receptor for viruses binding and entry and activate T helper (Th1) immune responses, thereby being applied to a vaccine composition against PRRSV.

The terms "recombinant protein", "chimeric protein", "recombinant antigen", "protein", "peptide" and "polypeptide", as used interchangeably herein, refer to a polymeric form of amino acids generally linked by peptide bonds or disulfide bonds. The "peptide" can also apply to amino acids in which one or more amino acid residues are naturally occurring amino acids and their polymers, or amino acid polymers having analogs or mimetics of corresponding naturally occurring counterparts. The "peptide" can further include modified amino acid polymer, for example, glycoprotein having carbohydrate residues, or phosphorylated peptide. The peptide, polypeptide and protein can be produced by liquid phase synthesis, solid phase synthesis, or using genetic engineering, recombinant cells, prokaryotic expression systems, eukaryotic expression systems.

The terms "amino acid" and "residue" can be used interchangeably herein. When the amino acid and the residue are used in combination, the amino acid residue refers to a naturally occurring and synthetic amino acid, an amino acid analog, an amino acid mimetic, and a non-naturally occurring amino acid chemically similar to the naturally occurring counterpart.

There is no limitation to the strains of PPRSV recited herein, which can be PPRSV-1, PPRSV-2 or other PPRSV strains. In an embodiment, the PPRSV strain can be PPRSV-2, for example.

The "recombinant antigen of porcine reproductive and respiratory syndrome virus (also called as PPRSV recombinant antigen or recombinant antigen)" recited herein, refers to a chimeric protein of different functional sequences, for example, PRRSV dual structural proteins and T-cell epitope. In an embodiment, the PRRSV dual structural proteins refer to a sequence consisting of ORF6 partial sequence in the N terminus and ORF5 complete sequence in the C terminus. In some examples, the PPRSV recombinant antigen can be consisted of an amino acid sequence listed as SEQ ID NO:1 with ORF6 partial sequence—ORF5 complete sequence—T-cell epitope from the N terminus to the C terminus, for example. In another embodiment, the PPRSV recombinant antigen can be an amino acid sequence of GP64 signal peptide—ORF6 partial sequence—ORF5 complete sequence—T-cell epitope from the N terminus to the C terminus. In other embodiment, a linker containing three to ten amino acids can be optionally disposed between two adjacent functional sequences, for example, between the GP64 signal peptide and the ORF6 partial sequence, between the ORF6 partial sequence and the ORF5 complete sequence, between the ORF5 complete sequence and the T-cell epitope. In addition, the PPRSV recombinant antigen can optionally include a His tag for facilitating its subsequent purification.

The "ORF5 complete sequence" recited herein refers to a glycoprotein GP5 having 191 amino acids, for examples.

The "ORF6 partial sequence" recited herein refers to a membrane protein (M protein) having a partial sequence of the $1^{st}$ to the $175^{th}$ amino acid, for example.

The "T-cell epitope" can have one or more copies, and there is no limitation to its copy numbers. In an embodiment, the T-cell epitope can have at least one copy.

It should be noted that, the aforementioned PRRSV recombinant antigen is designed according to specific sequences and arranged in specific order, so that the PRRSV recombinant antigen can achieve the effects of promoting polarization of PAMs, reducing receptor CD163 expression that is mediated for viral entry and activating Th1 immune responses and/or PRRSV resistance. If a recombinant protein was produced by a modified amino acid sequence instead of SEQ ID NO:1, for example, changing the selected sequence range or altering the order in which these sequences will be joined together, the recombinant protein having such modified amino acid sequence could not achieve the desired effects of promoting pro-inflammatory M1-phenotype polarization of PAMs, reducing receptor CD163 expression that is mediated for viral entry and activating Th1 immune responses and/or PRRSV resistance and the like.

In some embodiments, an immunogenic composition against PRRSV can include the aforementioned PRRSV recombinant protein. In other embodiments, the immunogenic composition against PRRSV can include an isolated polynucleotide, which is a recombinant gene sequence of PRRSV recombinant protein A1. In some examples, the aforementioned isolated polynucleotide is a polynucleotide sequence listed as SEQ ID NO: 2, for encoding an amino acid sequence listed as SEQ ID NO: 1.

In some embodiment, the aforementioned immunogenic composition can be an immunogenic composition for promoting polarization of a PAM, an immunogenic composition for activating Th1 immune responses, and/or a vaccine composition against PRRSV, for example.

"Polarization status of porcine alveolar macrophages (PAMs)" discussed herein determines the infectivity of porcine reproductive and respiratory syndrome virus (PRRSV). PRRSV infection may skew macrophages polarization towards an M2 phenotype followed by T cells inactivation. CD163, one of the scavenger receptors on M2 macrophages, has been known as a putative receptor of PRRSV involving in virus uncoating. In some embodiments, the polarization status of PAMs can be assessed according to increasing levels of gene transcription product of pro-inflammatory cytokines (e.g., TNF-α, IL-6 and IL-12).

"Activation of T helper (Th1) immune responses" discussed herein refers to the ability of activating T cells, which can be assessed according to activating levels of both T-cell receptor (TCR) signaling pathway and estrogen receptor signaling pathway.

In some embodiments, two types of PRRSV-derived recombinant antigens A1 (also called as g6Ld10T) and A2 (also called as lipo-M5Nt, consisting of lipopeptide—ORF6 partial sequence—ORF5 partial sequence—ORF7 partial sequence), for testing their capabilities to mediate PAMs polarization and Th1 cells activation. In some embodiments, CD163 expression on PAMs was significantly decreased after being challenged with PRRSV recombinant antigen A1, but significantly increased with PRRSV recombinant antigen A2. The gene transcripts of pro-inflammatory cytokines, such as TNF-α, IL-6, and IL-12, were significantly increased in PAMs challenged with PRRSV recombinant antigen A1. In addition, data from Next GenerationSequencing (NGS) not only support the evidences in parallel, but also show an increase in T cells receptor signaling pathway in PAMs challenged with PRRSV recombinant antigen A1 instead of that with PRRSV recombinant antigen A2. By using co-culture system, PAMs challenged with PRRSV recombinant antigen A1, but not PRRSV recombinant antigen A2, can induce T helper (Th1) activation by increasing secretion of IFN-γ and IL-12, as well as boosting upregulation of TNF-α and IL-6 gene expression, respectively. The activation of Th1 cells potentially affects the subsequent activation of humoral immune cells (i.e., antibody production). In view of innate and T cells-mediated immunity, PRRSV recombinant antigen A1 is potentially regarded as an effective ingredient of an immunogenic composition and/or a vaccine for providing immunization for PRRSV infection by its capacity to revert the polarization status of PAMs from immunosuppressive to pro-inflammatory phenotypes, which in turn reduces the expression of CD163 receptor for viral entry and increases the immunomodulation for Th1 type response. In some embodiments, PRRSV recombinant antigen A1 can be made to a subunit vaccine and/or a nucleic acid-based vaccine (e.g., DNA vaccine, viral vector vaccine).

Thereinafter, it will be understood that particular recombinant protein sequences, specific formulations, specific detecting methods, aspects, examples and embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1

1.1 Pigs and Inoculations

Ethics statement: The lung collection and the pig euthanization in the following EXAMPLES were approved by the Institutional Animal Care and Use Committee (IACUC) of Veterinary Medicine at National Pingtung University of Science and Technology (NPUST), Taiwan.

This EXAMPLE was performed on specific pathogen free (SPF) piglets, approximately eight to eleven weeks of age and nine to twelve kg in weight. These piglets were raised in the room with positive pressure in NPUST Animal Diagnostic Center.

1.2 Construction of Recombinant Protein Antigen

The amino acid sequence of the recombinant antigen 1 (A1) was listed as SEQ ID NO:1, which was constructed from GP64 signal peptide (40 a.a.), ORF6 partial sequence (the $1^{st}$ to the $175^{th}$ amino acid of M protein, total 175 a.a.), ORF5 complete sequence (the $11^{st}$ to the $201^{st}$ amino acid of glycoprotein GP5, total 191 a.a.) and several copies of T-cell epitopes from the N terminus to the C terminus. The DNA sequence of the recombinant antigen 1 (A1) was listed as SEQ ID NO:2, which could express the recombinant antigen 1 using a baculovirus expression system.

The amino acid sequence of the recombinant antigen 1 (A2) was listed as SEQ ID NO:3, which was constructed from lipopeptide (40 a.a.), ORF6 partial sequence (the $2^{nd}$ to the $27^{th}$ amino acid of M protein), ORF5 partial sequence (the $31^{st}$ to the $63^{rd}$ amino acid of glycoprotein GP5) and ORF7 partial sequence (the $42^{nd}$ to the $123^{rd}$ a.a. of N protein) from the N terminus to the C terminus, and expressed using *E. coli* expression system.

Commercially available products could be used in the aforementioned baculovirus expression system and the *E. coli* expression system rather than specific limitations. These expression systems were well known by the person skilled in this art without further detailed description.

1.3 Collecting Porcine Alveolar Macrophages (PAMs)

Pigs were euthanized by exsanguination. The trachea was ligated to prevent pneumothorax (i.e., total pulmonary collapse), followed by the removal of heart and lungs from the thorax. Alveolar macrophages were harvested aseptically from fresh lungs. The lungs were washed intratracheally 2 to 4 times with phosphate buffered saline (PBS), and the wash fluids containing PAMs were centrifuged for 10 minutes at 300 xg of rotation speed. The collected PAMs were seeded in 24-well cell culture plates and maintaining with complete RPMI-1640 medium (Corning, Manassas, VA, USA) containing 10% fetal bovine serum (FBS) (Hyclone, Logan, UT, USA) at 37° C. in a humidified 5% $CO_2$ atmosphere.

1.4 Cytokine Stimulation

PAMs were seeded in 24-well cell culture plates and divided into five groups; Control (untreated); 10 ng/ml LPS (Sigma-Aldrich, Steinheim, Germany) added; 20 ng/ml IL-4 (BIOTECH, INC) added; 5 µg/ml of A1 added; and 5 µg/ml of PRRSV recombinant antigen A2 added. After 48 hours (h) of treatment, cells were collected to extract RNA and perform qPCR analyses.

1.5 RNA Extraction and Quantitative Real-Time Polymerase Chain Reaction

Total RNA was extracted using Trizol reagent (Invitrogen, Canada, USA) according to the manufacture's protocol. Total RNA (1 µg) was subjected to the reverse transcription (RT) reaction using iScript cDNA Synthesis Kit (Bio-Rad, Hercules, CA, USA). The quantitative real-time PCR was performed using KAPA SYBR® FAST qPCR Master Mix (2×) Kit (KAPA Biosystem, Wilmington, DE, USA) according to the manufacturer's protocol. Quantitative real-time PCR reactions were also performed using a QIAGEN Rotor Gene Q Real-Time PCR. The primer sequences (5'-3'; forward and reverse) were listed as SEQ ID NOs:4 to 13. The amplification steps were performed for 3 minutes at 95° C., followed by 40 cycles of denaturation at 95° C. for 3 seconds, and annealing at 60° C. for 20 seconds. The data were calculated using the standardized mRNA level comparative methods $2^{-\Delta\Delta Ct}$.

1.6 Flow Cytometry Analysis

PAMs ($1\times10^6$) were collected and washed once with PBS containing 0.5% BSA (Sigma-Aldrich, Steinheim, Germany). Cells were incubated with 1 µg of FITC-labelled SLA II$^+$ antibody (Bio-Rad), 5 µg of FITC-labelled CD14$^+$ antibody (Invitrogen), 0.1 µg of antigen-presenting cell-CD80$^+$ (APC-CD80$^+$) antibody (Invitrogen) and phycoerythrin-labelled CD163$^+$ (PE-CD163$^+$) antibody (diluted 1:10, Invitrogen) for incubating 20 minutes on ice in the dark. Next, the cells were rinsed with centrifugation 5 minutes at 300 xg, and resuspended in 500 µL to 1 mL of ice cold PBS. And then, cell surface proteins were measured by the flow cytometry (BD Biosciences, San Jose, CA, USA), and the analysis was performed using BD FACSDiva™ Software (BD Biosciences) and FlowJo Software (Tree Star, Inc., Ashland, OR, USA).

1.7 Next Generation Sequencing (NGS) Analysis

The RNA purification and cDNA synthesis were performed using commercially available mRNA Library Prep Kit [e.g., TruSeq Stranded mRNA Library Prep Kit (Illumina, San Diego, CA, USA)] according to manufacturers' protocols. cDNA libraries were assessed on commercial instruments of a microfluidic electrophoresis analyzer system (e.g., Agilent Bioanalyzer 2100 system) and a Real-Time PCR system. NGS was performed externally at the Genomics (Genomics, BioSci & Tech Company, New Taipei City, Taiwan) on an Illumina Novaseq 6000 with 150 base pairs (bp) paired-end reads. Raw-sequencing reads were filtered using program Trimmomatic (version 0.36). Read alignments were assembled using Bowtie2 (version 2.3.5). The raw gene counts were extracted with RSEM (version 1.3.3). The commercial R language software package (R package EdgeR v3.16.5 tool) was used for differential gene expression analysis between two sample groups. A gene ontology (GO) enrichment analysis was conducted on the differential genes obtained through screening, and when $p<0.05$, the GO terminology was regarded as significantly enriched. The Kyoto Encyclopedia of Genes and Genomes (KEGG, https://www.genome.jp/kegg/kegg2.html) was used for gene enrichment of differentially expressed genes. The datasets presented in this study could be found in online repositories (NCBI Bioproject PRJNA665327: https://dataview.ncbi.nlm.nih.gov/object/PRJNA726625), assessed on 1 May 2021.

1.8 Integration of the Protein-Protein Interaction (PPI) Network

The potential differential expression gene (DEG) interactions at the protein level were explored by the Search Tool for the Retrieval of Interacting Genes (STRING; string-db.org). The PPI networks of DEGs by STRING were derived from validated experiments. $P<0.05$ was considered to indicate a statistically significant difference.

1.9 Peripheral Blood Mononuclear Cells (PBMCs)

Peripheral blood mononuclear cells (PBMCs) were centrifuged at the rotation speed of 400 xg for 30 minutes and collected using Ficoll-Paque™ (GE Healthcare BioSciences, Uppsala, Sweden) density gradient centrifugation according to the manufacturer's indications. PBMCs were rinsed thrice with RPMI 1640 medium (Corning, Manassas, VA, USA), and these cells were resuspended in advanced RPMI 1640 medium containing 10% fetal bovine serum (FBS; Hyclone, Lo-gan, UT, USA) for subsequent experimentations.

1.10 T Cells Subsets Sorted by Fluorescence Activated Cell Sorting (FACS)

For the purpose of obtaining T cells subsets, PBMCs were sorted into several subsets by FACS for co-culture experiments. Briefly, cells ($1\times10^6$ cell/mL) were stained by 0.05 µg of anti-porcine FITC-CD4$^+$ antibody (Ab24989, Abcam, Cambridge, UK) and 10 µg of anti-porcine CD25$^+$ primary antibody (MCA1736GA, Bio-Rad) and incubated on ice for 30 minutes in the dark. Next, the cells were stained by 5 µg of mouse R-phycoerythrin (R-PE) conjugated IgG1 secondary antibody (STAR132PE, Bio-Rad) and incubated on ice for 30 minutes in the dark. Later, the stained cells were rinsed twice with cold PBS before subjection to BD FACS Aria II flow cytometer (BD Biosciences, USA). The T cells were divided into two subsets (T1 and Treg, respectively) according to expressions of $CD4^+CD25^-$ (Th1) and $CD4^+CD25^+$ (Treg).

1.11 Th1 Cytokine Analysis

Firstly, $2\times10^6$ cell/mL of PAMs seeded on the bottom of the lower chamber of the indirect transwell co-culture system and incubated overnight. Next, the cells in the lower chamber were stimulated by PRRSV recombinant protein A1 or PRRSV recombinant protein A2, and the T cell subsets ($CD4^+CD25^-$ or $CD4^+CD25^+$) were simultaneously seeded on the membrane of the upper chamber. And then, the transwell co-culture system was incubated under a standard condition (5% $CO_2$, 37° C.) for 48 hours. Later, the conditioned media were collected for analyzing Th1 cytokines.

Briefly, a standard curves of concentrations of cytokines IFN-γ and IL-12 were established using a commercial ELISA kit of IFN-γ (Thermo Fisher Scientific, Vienna, Austria) and IL-12 (R&D System, USA), according to the manufacturer's method. Next, the optical density at 450 nm ($OD_{450\ nm}$) of each well was determined by commercial Microplate Reader (EZ Read 400 Microplate Reader, Biochrom, Cambridge, UK). In addition, the expressions of pro-inflammatory cytokines TNF-α, IL-6 and Arg-1 were detected by real-time quantitative PCR.

1.12 Statistical Analysis

Data were presented as mean±SEM when indicated. Statistical analysis was conducted by t-test with a 95% confidence limit, and one-way ANOVA followed by Tukey's test for multi comparisons. The data analysis was performed using Prism 7.0 (GraphPad Software Inc., USA). Differences were considered significant at P<0.05.

Example 2: Evaluation of PPRSV Recombinant Antigen 1 (A1) Driving PAMs to M1 Macrophage Polarization and Downregulating the Expression of CD163 on PAMs Reference was made to FIGS. 1A and 1B, which illustrated the expressions of surface markers of PAMs from PRRSV infected animals according to an embodiment of the present invention, which respectively illustrated the bar charts of cell percentages (FIG. 1A) and mean fluorescence intensity (MFI, FIG. 1B) of CD14, SLA II, CD80 and CD163-positive cells detected using specific monoclonal antibodies, FITC-conjugated anti-mouse antibodies and flow cytometry. The expressions of PAMs from the uninfected animals were used as control.

Figure 1B:
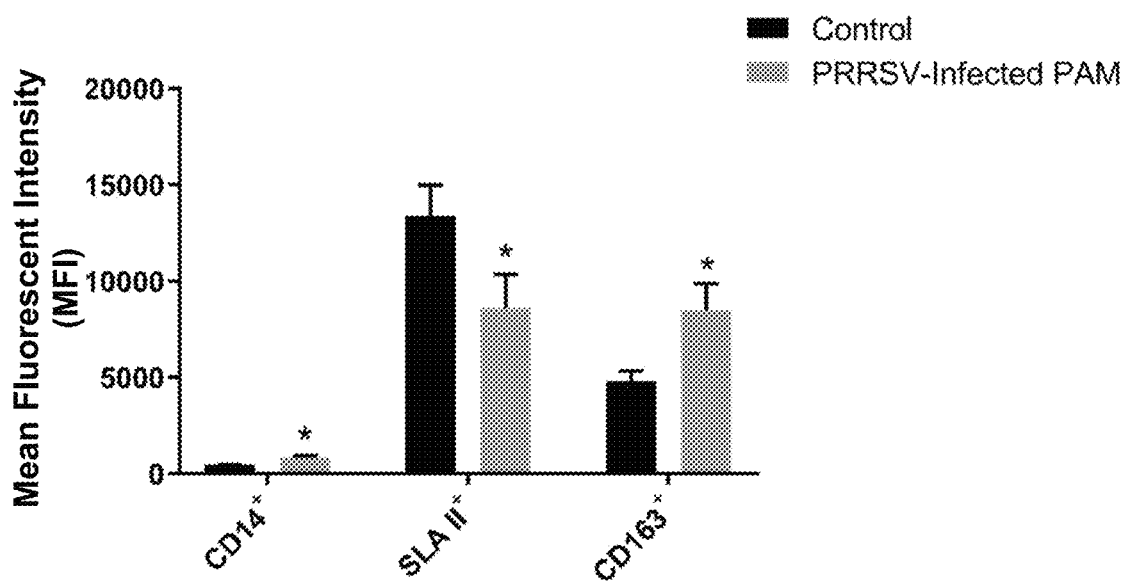

Since PAMs represented the PRRSV target cells in pigs, this EXAMPLE was firstly to determine the specific markers associated with these cells. Among them, CD14 was earlier investigated as a marker of the myelomonocytic phenotype. Moreover, PAMs were known to express SLA II and CD163 receptors. Cells expressing CD14, SLA II, CD163 positively were found in 91.3%, 97.5%, and 95.2% PAMs isolated from healthy pigs. On the contrary, only a small percentage of cells (23.8% and 23.1%) expressing CD14 and CD163 were found in PAMs isolated from PRRSV-infected pigs. While there were no significant differences between health and PRRSV-infected pigs, there was a trend for decreased the percentage of cells-expressing SLA II (85.8%) (FIG. 1A). Nevertheless, the mean fluorescence intensity (MFI) of CD163 was significantly higher in PAMs isolated from PRRSV-infected pigs, indicating that PRRSV-infected PAMs drove to M2-phenotype polarization, the average expression of CD163 receptor in this cell lineage was upregulated, and CD163 receptor played an important role for this receptor in this cell lineage suffering PRRSV infection (FIG. 1B).

Figure 2A:
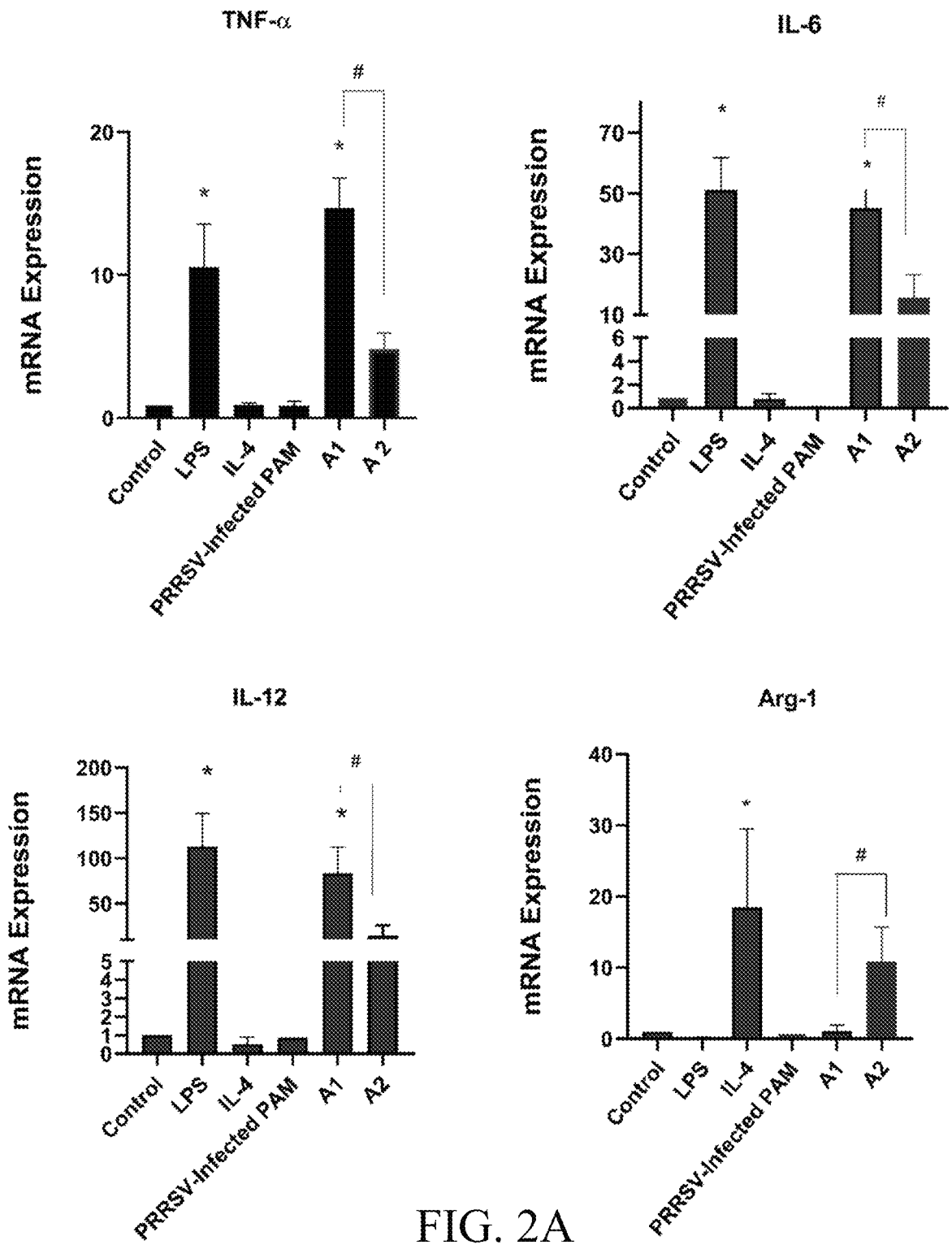
FIG. 2A illustrates the bar chart of mRNA expression of M1 PAMs and M2 PAMs challenged with PRRSV recombinant antigen according to an embodiment of the present invention.
Figure 2B:
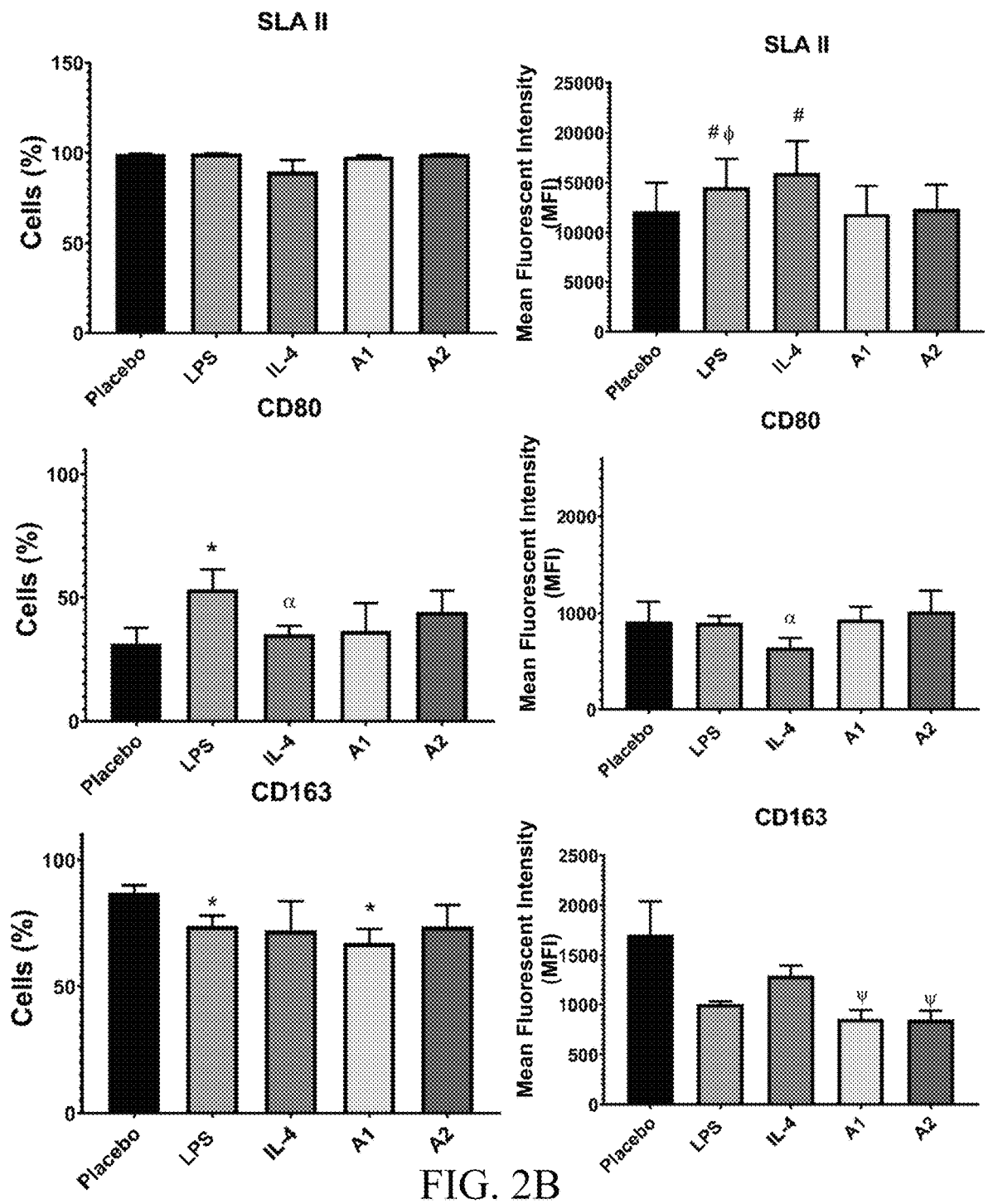
FIG. 2B illustrates the bar chart of the expressions of surface proteins SLA II, CD80 and CD163 of PAMs analyzed by flow cytometry according to an embodiment of the present invention.

Reference was made to FIGS. 2A and 2B, which illustrated PPRSV recombinant antigen 1 (A1) driving M1 macrophage polarization and decreasing the expression of CD163 on PAMs according to an embodiment of the present invention. FIG. 2A illustrates the bar chart of mRNA expression of M1 PAMs and M2 PAMs challenged with PRRSV recombinant antigen according to an embodiment of the present invention, which was detected by quantitative PCR (qPCR). As shown in the result of FIG. 2A, PPRSV recombinant antigen 1 (A1) could upregulate expression of pro-inflammatory gene mRNA, but downregulate expression of anti-inflammatory genes. FIG. 2B illustrated the bar chart of the expressions of surface proteins SLA II, CD80 and CD163 of PAMs analyzed by flow cytometry according to an embodiment of the present invention. PPRSV recombinant antigen 1 (A1) could reduce cell percentages and MFI of CD163 expressing PAMs. PAMs were treated with LPS, IL-4, PPRSV recombinant antigen 1 (A1) or PPRSV recombinant antigen 2 (A2) for 48 hours. Untreated PAMs were used as control. The symbol * represented as p<0.05 compared to the control group; the symbol a represented as p<0.05 compared to the LPS group; the symbol ψ represented as p<0.05 compared to the IL-4 group; the symbol #represented as p<0.05 compared to the A1 group; the symbol φ represented as p<0.05 compared to the A2 group. The data were analyzed by mean±SEM, calculated from 3 pigs (duplicate each pig).

To further validate the effect of antigens on macrophages polarization, in this EXAMPLE, PAMs were challenged with PRRSV recombinant antigens (A1 and A2). The results showed that PAMs challenged with PRRSV recombinant antigen A1 enhanced the upregulation of pro-inflammatory genes (TNF-α, IL-6 and IL-12), suggesting that PRRSV recombinant antigen A1 promotes M1 macrophages polarization, but not in PAMs challenged with PRRSV recombinant antigen A2. In contrast, PRRSV recombinant antigen A2-challenged PAMs upregulated the expression of Arg-1, one of the anti-inflammatory genes representative for M2 macrophages (FIG. 2A). There were no significant differences on SLA II surface protein marker between PRRSV recombinant antigen A1 and PRRSV recombinant antigen A2 induction. However, the number and MFI of expressing CD163 cells were significantly decreased after they were treated with PRRSV recombinant antigen A1 (FIG. 2B). These results suggested that PRRSV recombinant antigen A1 could regulate macrophages polarization and a candidate for inhibiting PRRSV infection.

Figure 3A:
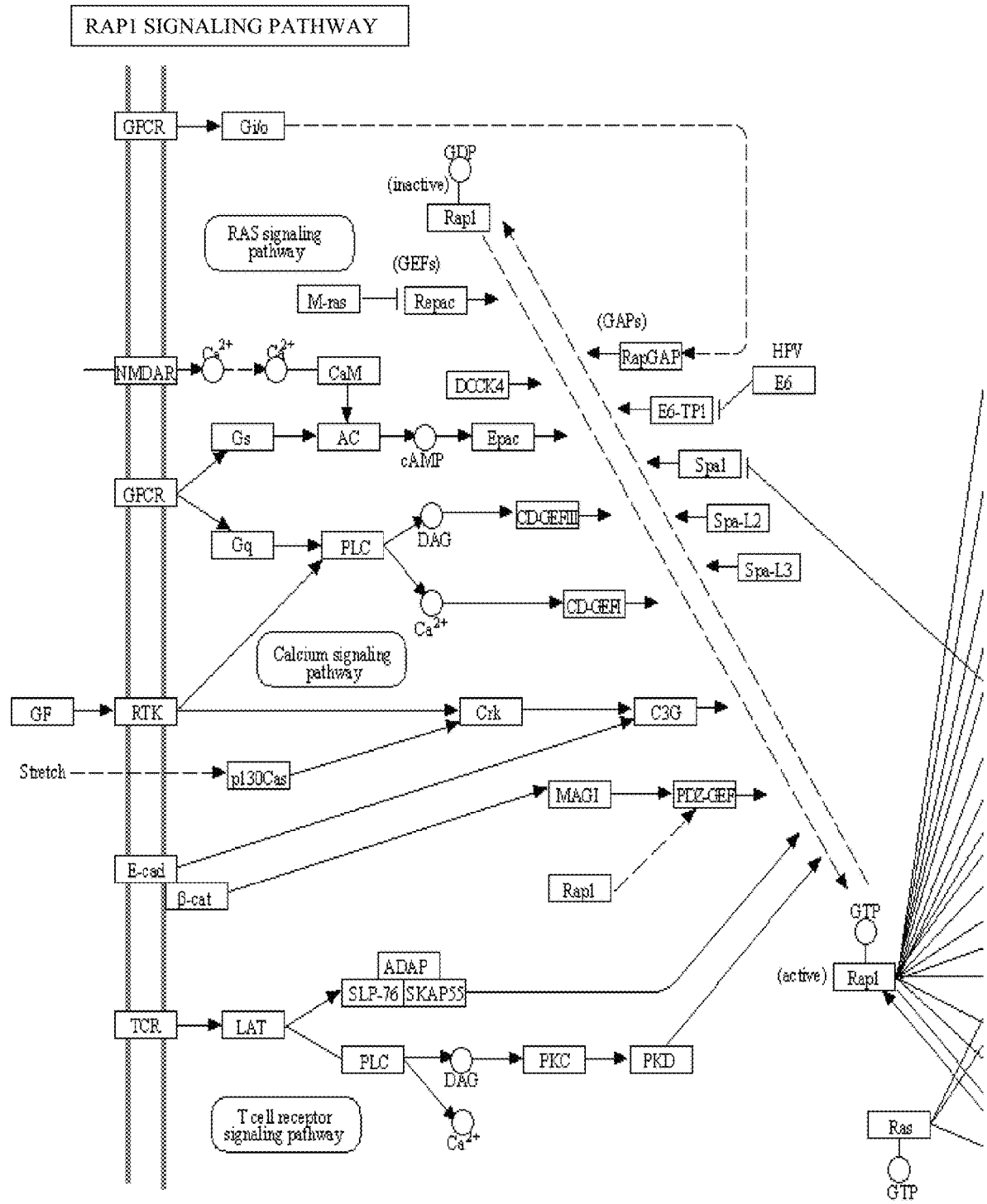
FIGS. 3A and 3B illustrate a predicted result (the left part shown in FIG. 3A and the right part shown in FIG. 3B) of Rap1 signaling pathway involving in TCR signaling pathway activation according to an embodiment of the present invention.
Figure 3B:
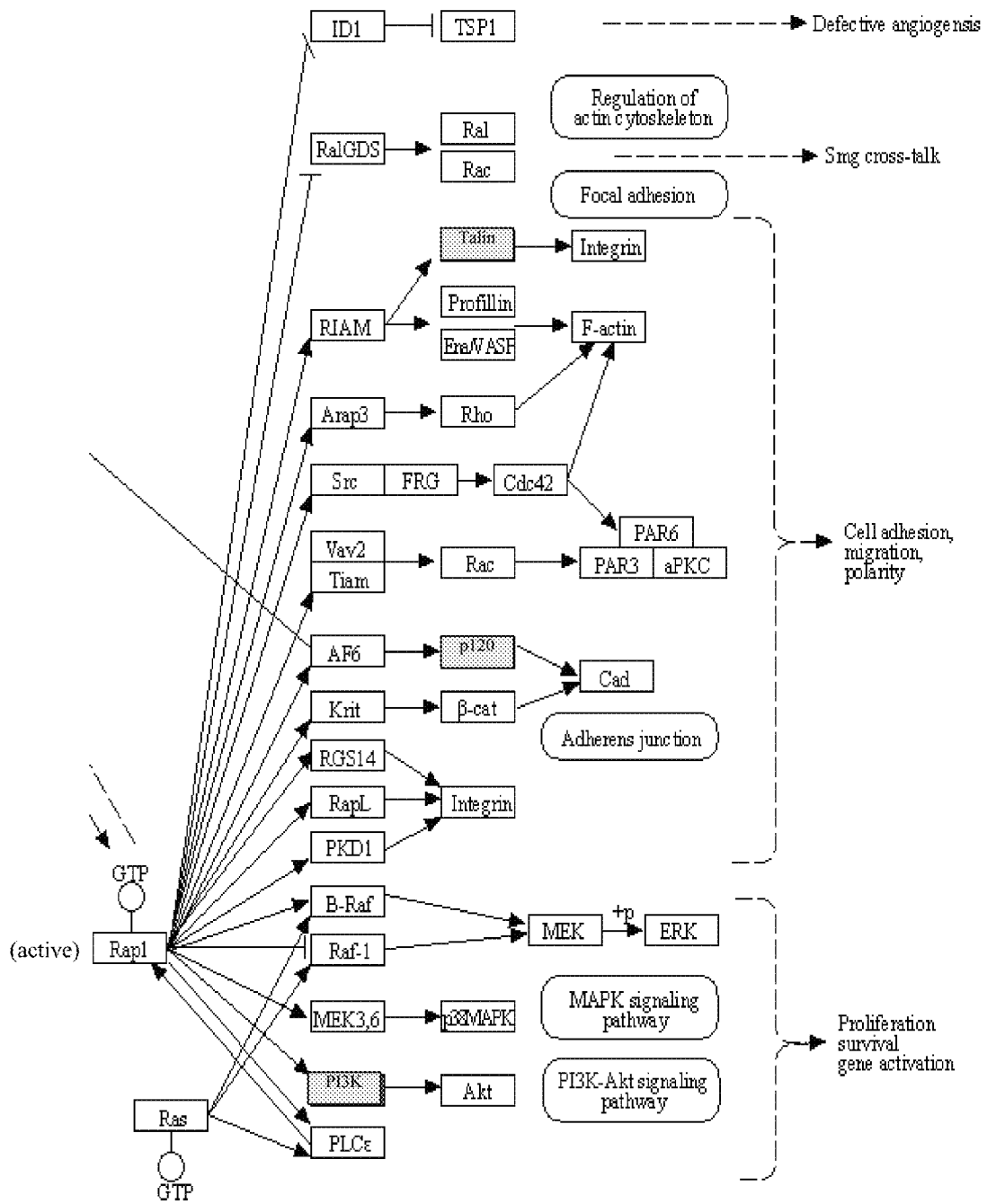

Reference was made to FIGS. 3A and 3B, which illustrated a predicted result (the left part shown in FIG. 3A and the right part shown in FIG. 3B) of Rapt signaling pathway involving in TCR signaling pathway activation according to an embodiment of the present invention, thereby enhancing proliferation, survival and gene activation. T cell receptors (TCRs) signaling pathway was enriched only in up-regulated genes, which were promoted by PRRSV recombinant antigen A1. It was similarly found that C-type lectin receptors (CLRs) signaling pathway were also enriched. CLRs could promote various signaling pathways and potentially activate transcription factors NF-κB, leading to the expression of specific cytokines that determine T cell differentiation status, and thus it was one of important designs of vaccine development. To investigate the potential protein-level interactions of differentially expressed genes (DEG) in regulating the immune response, this EXAMPLE generated an analysis of predicted protein-protein interactions (PPI) of differentially expressed genes using Search Tool for Retrieval of Interacting Genes (STRING) analysis. As shown in the result of FIGS. 3A and 3B, some proteins secreted by PAMs challenged by PRRSV recombinant antigen A1 were correlated with inflammatory and immune responses, such as caspase1, IL18, PIK3CB, and IKKB.

Figure 4A:
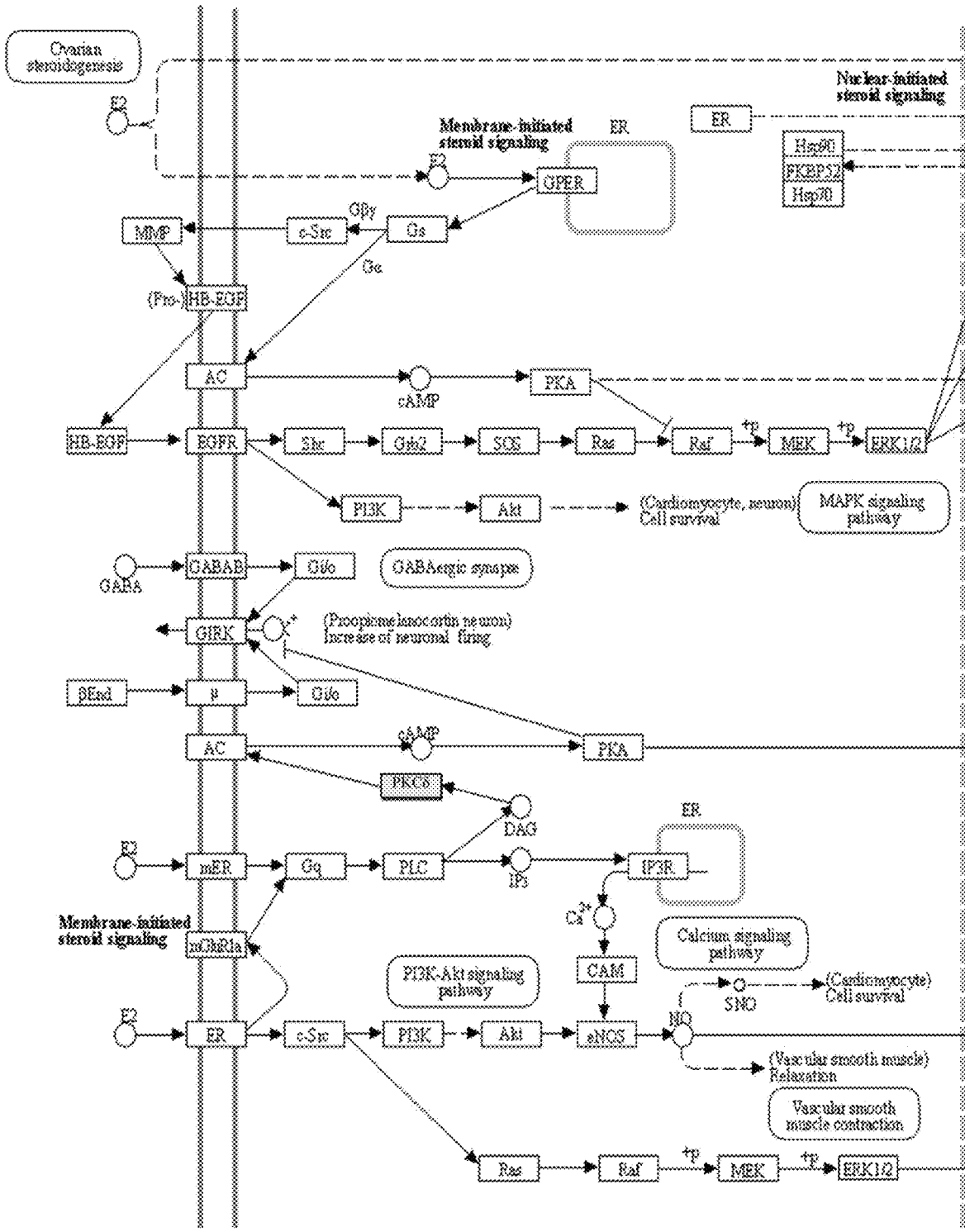
FIGS. 4A and 4B illustrate a predicted result (the left part shown in FIG. 4A and the right part shown in FIG. 4B) of Estrogen signaling pathway according to another embodiment of the present invention.
Figure 4B:
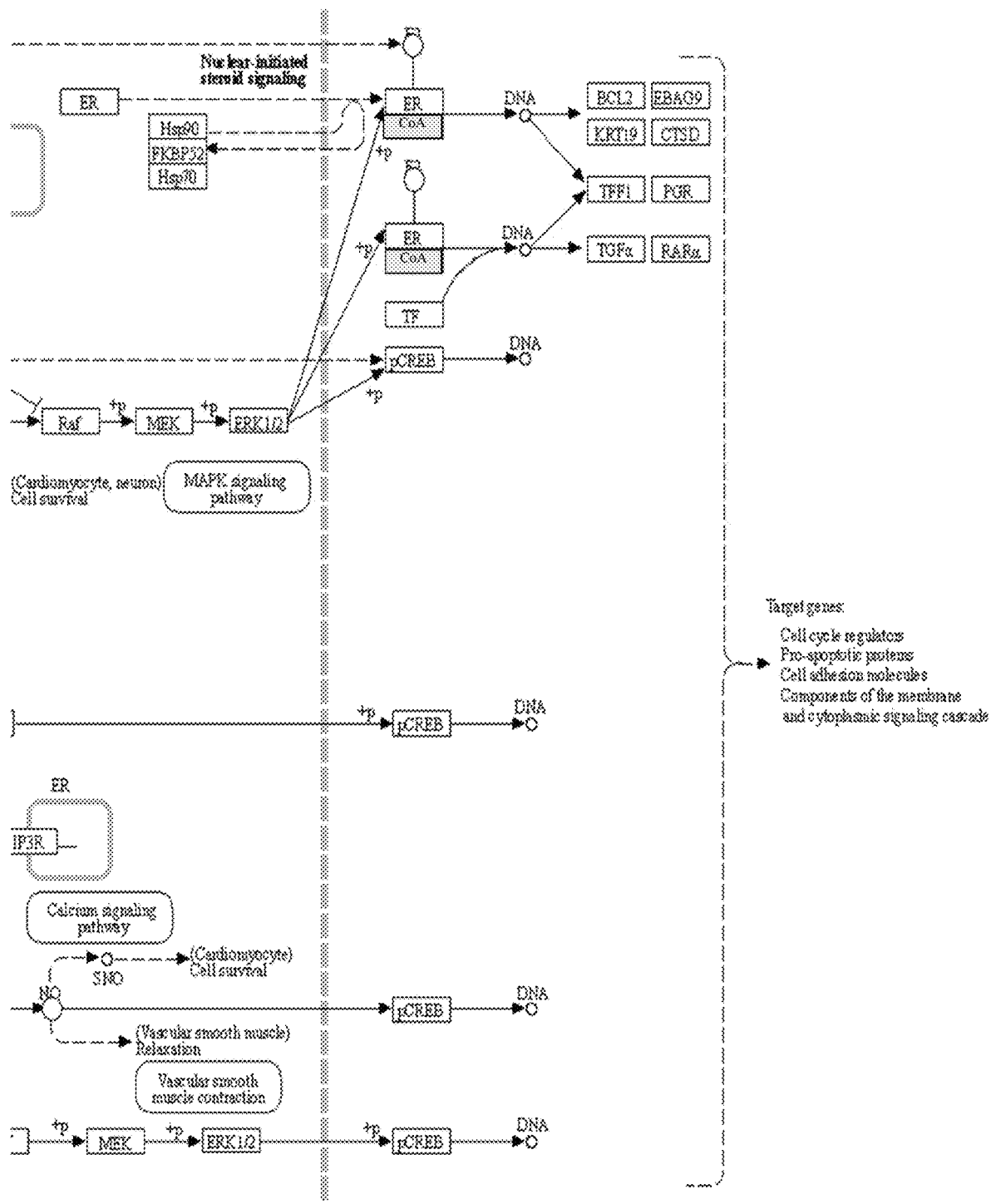

Reference was made to FIGS. 4A and 4B, which illustrated a predicted result (the left part shown in FIG. 4A and the right part shown in FIG. 4B) of Estrogen signaling pathway according to another embodiment of the present invention, for involving in the activation of TCR signaling pathway. As the analysis result of KEGG mapping tool in FIGS. 4A and 4B, the downregulation of anti-inflammatory genes was associated with suppressing estrogen signaling, and estrogen could stimulate the M2 macrophage polarization during the skin healing process. In addition, these genes could stimulate proteins of regulation T-cell activation, for example, SG15, CYLD and DAPK1 (data not shown).

Isolated PAMs were challenged with antigens followed by co-cultured with $CD4^+CD25^+$ Tregs or $CD4^+CD25^-$Th1 cells for 48 hours. Cytokine protein concentrations were measured by ELISA and determined by mean±SEM, calculated from 3 pigs (duplicate each pig), and the results were shown in FIGS. 5A to 5E, in which the symbol * represented as p<0.05 compared to PAMs group.

Figure 5A:
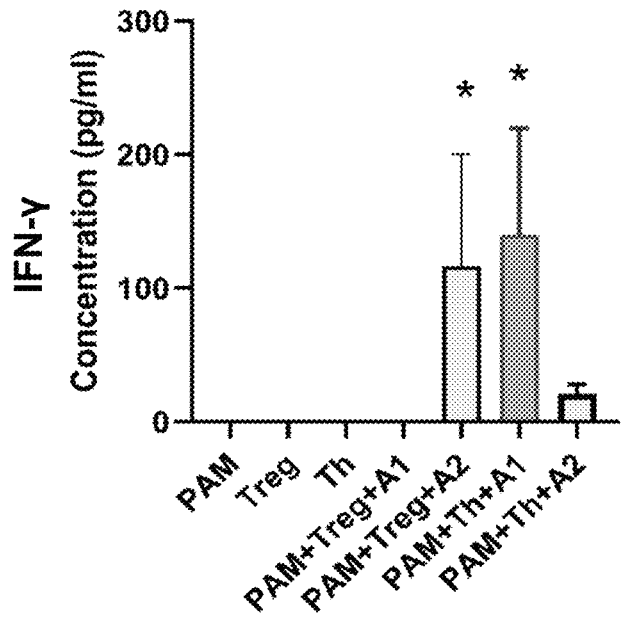
FIGS. 5A to 5E illustrates the bar charts of the expression of detected pro-inflammatory cytokines and genes according to an embodiment of the present invention.
Figure 5B:
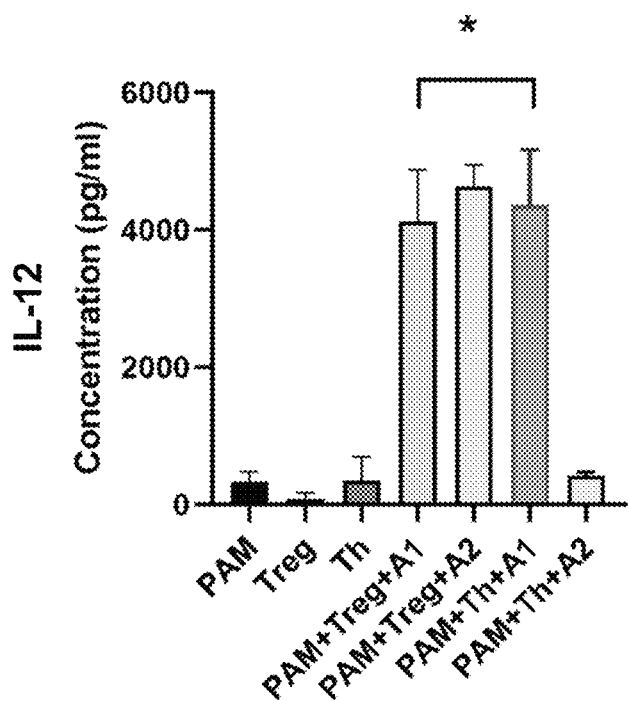
Figure 5C:
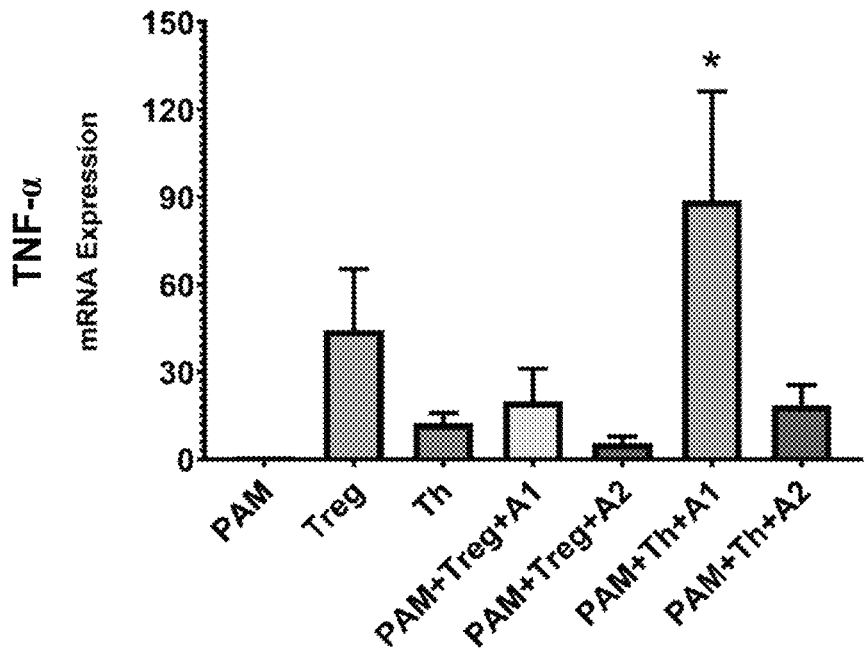
Figure 5D:
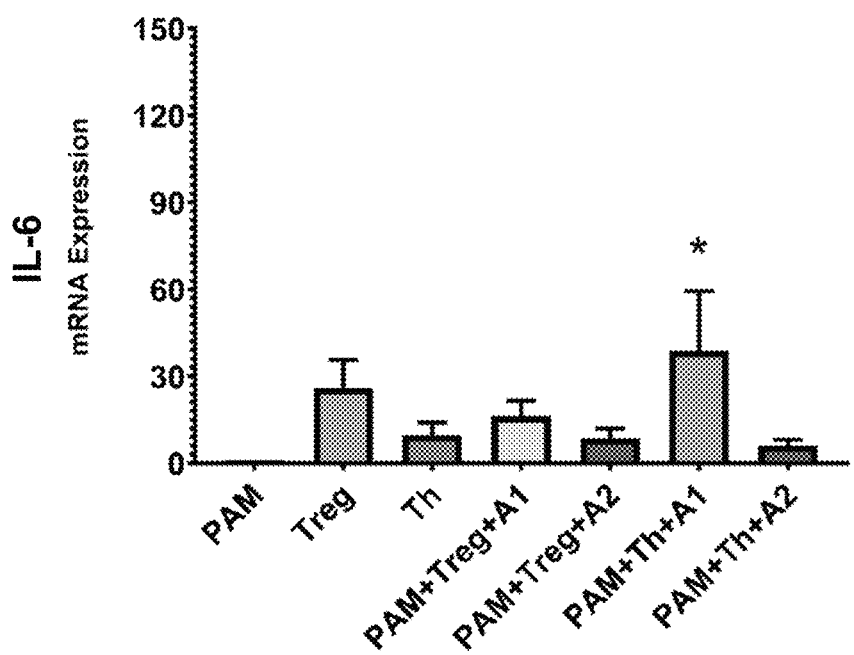
Figure 5E:
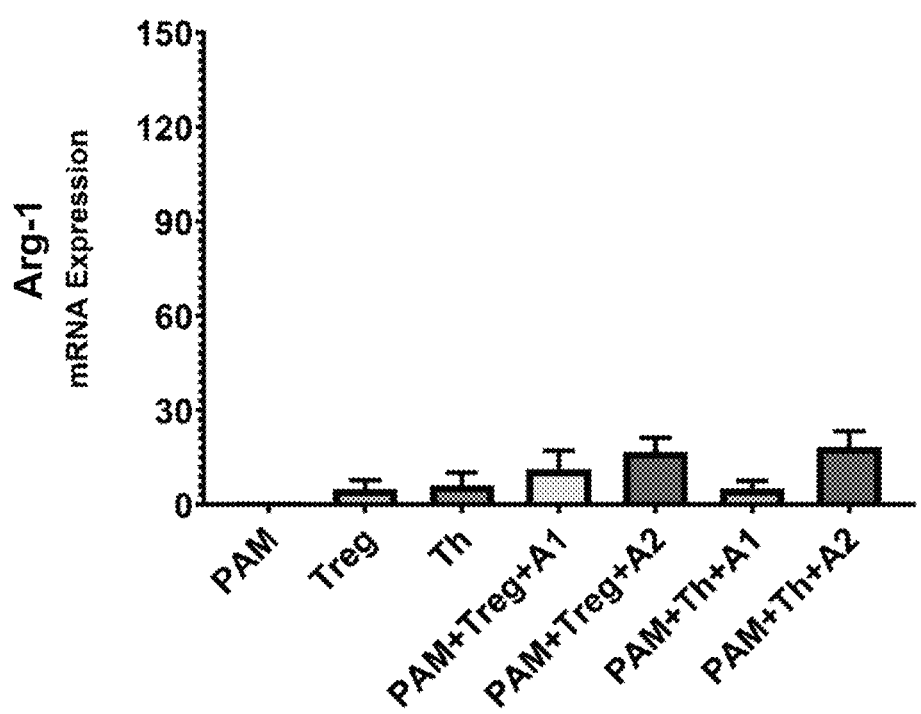

Reference was made to FIGS. 5A to 5E, which illustrated the bar charts of the expression of detected pro-inflammatory cytokines and genes according to an embodiment of the present invention. As shown in the real-time quantitative RT-PCR analysis, PRRSV recombinant antigen A1-challenged PAMs cocultured with Th1 increased the secretion levels of IFN-γ (FIG. 5A) and IL-12 (FIG. 5B). In addition, PRRSV recombinant antigen A1-challenged PAMs cocultured with Th1 also boosted the mRNA expression of TNF-α (FIG. 5C) and IL-6 (FIG. 5D), but showed no significant differences in Arg-1 expression (FIG. 5E).

In summary, the aforementioned specific amino acid sequences, specific processes, specific compositions, specific analysis models or specific evaluation methods were only exemplary to describe the recombinant antigen and the isolated polynucleotide of PRRSV, the composition including the same and the method of making the same. However, those of common knowledge in the technical field of the present invention should understand that other amino acid sequences, other processes, other compositions, other analysis models or other evaluation methods, etc., also can be applied to the recombinant antigen and the isolated polynucleotide of PRRSV, the composition including the same and the method of making the same, without limiting to the aforementioned description of the present invention. For example, the recombinant antigen can be produced by other processes for optimizing the process and the mass production.

According to the aforementioned embodiments, in the recombinant antigen and the isolated polynucleotide of PRRSV, the composition including the same and the method of making the same of the present invention, the recombinant protein expressed by the polynucleotide in an eukaryotic expression system can be advantageous for mass production and purification. An immunogenic composition including the recombinant antigen can promote pro-inflammatory M1-phenotype polarization of PAMs, reduce receptor CD163 expression mediated for viral entry and activate T helper (Th1) immune responses, thereby being beneficially applied to a vaccine composition against PRRSV in future.

Although the present invention has been described in considerable detail with reference to certain embodiments thereof, other embodiments are possible. Therefore, the spirit and scope of the appended claims should not be limited to the description of the embodiments contained herein.

What is claimed is:

1. An immunogenic composition, comprising a porcine reproductive and respiratory syndrome virus (PRRSV) recombinant antigen as an effective ingredient, wherein the PRRSV recombinant antigen consists of the amino acid sequence set forth in SEQ ID NO: 1.

2. The immunogenic composition of claim 1, wherein the immunogenic composition is an immunogenic composition against the PRRSV.

3. The immunogenic composition of claim 1, wherein the immunogenic composition is a vaccine composition against the PRRSV.

4. The immunogenic composition of claim 1, wherein the immunogenic composition is an immunogenic composition for promoting polarization of a porcine alveolar macrophage (PAM).

5. The immunogenic composition of claim 4, wherein the PAM is classified into a pro-inflammatory M1 phenotype.

6. The immunogenic composition of claim 1, wherein the immunogenic composition is an immunogenic composition for activating T helper (Th1) immune responses.

7. The immunogenic composition of claim 6, wherein the immunogenic composition reduces receptor CD163 expression.

8. An immunogenic composition comprising an isolated polynucleotide as an effective ingredient, wherein the isolated polynucleotide consists of the nucleotide sequence set forth in SEQ ID NO: 2 and encodes the amino acid sequence set forth in SEQ ID NO: 1.

9. The immunogenic composition of claim 8, wherein the immunogenic composition is an immunogenic composition against PRRSV.

10. The immunogenic composition of claim 8, wherein the immunogenic composition is a vaccine composition against PRRSV.

11. The immunogenic composition of claim 8, wherein the immunogenic composition is an immunogenic composition for promoting polarization of a PAM.

12. The immunogenic composition of claim 11, wherein the PAM is classified into a pro-inflammatory M1 phenotype.

13. The immunogenic composition of claim 8, wherein the immunogenic composition is an immunogenic composition for activating T helper (Th1) immune responses.

14. The immunogenic composition of claim 13, wherein the immunogenic composition reduces receptor CD163 expression.

15. A method of making a recombinant antigen of PRRSV, comprising:
   transfecting the polynucleotide set forth in SEQ ID NO: 2 into an eukaryotic expression system;
   culturing the transfected eukaryotic expression system for expressing the recombinant antigen, wherein the recombinant antigen consists of the amino acid sequence set forth in SEQ ID NO: 1; and
   purifying a cultured supernatant of the transfected eukaryotic expression system, for obtaining the recombinant antigen.

16. The method of claim 15, wherein the eukaryotic expression system is a baculovirus expression system.

* * * * *